(12) United States Patent
Bossenmaier et al.

(10) Patent No.: US 7,205,325 B2
(45) Date of Patent: Apr. 17, 2007

(54) OXAZOLE DERIVATIVES

(75) Inventors: Birgit Bossenmaier, Seefeld (DE); Walter-Gunar Friebe, Mannheim (DE); Thomas Friess, Planegg (DE); Bernhard Goller, Penzberg (DE); Matthias Rueth, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 499 days.

(21) Appl. No.: 10/808,935

(22) Filed: Mar. 25, 2004

(65) Prior Publication Data

US 2004/0209933 A1    Oct. 21, 2004

Related U.S. Application Data

(60) Provisional application No. 60/459,741, filed on Apr. 2, 2003.

(30) Foreign Application Priority Data

Mar. 28, 2003    (EP) .................... 03007124

(51) Int. Cl.
A61K 31/4192 (2006.01)
C07D 249/04 (2006.01)

(52) U.S. Cl. .................. 514/374; 548/255; 548/247

(58) Field of Classification Search ............ 548/255, 548/247; 514/374
See application file for complete search history.

(56) References Cited

U.S. PATENT DOCUMENTS

| 4,448,781 | A | 5/1984 | Cross et al. |
| 5,281,593 | A | 1/1994 | Gilmore et al. |
| 5,322,847 | A | 6/1994 | Marfat et al. |
| 5,410,061 | A | 4/1995 | Gilmore et al. |
| 5,482,954 | A | 1/1996 | Kohn et al. |
| 5,684,022 | A | 11/1997 | Shuto et al. |
| 5,776,932 | A | 7/1998 | Schindler et al. |
| 5,883,106 | A | 3/1999 | Stevens et al. |
| 6,156,748 | A | 12/2000 | Panetta et al. |
| 6,211,215 | B1 | 4/2001 | Momose et al. |
| 6,716,863 | B2* | 4/2004 | Tasaka et al. ............ 514/374 |

FOREIGN PATENT DOCUMENTS

| DE | 196 10 882 A1 | 9/1997 |
| EP | 0 029 742 A1 | 6/1981 |
| EP | 0 335 144 A1 | 10/1989 |
| EP | 1270571 | 1/2003 |
| WO | WO 97/00249 A1 | 1/1997 |
| WO | WO 98/03505 | 1/1998 |
| WO | WO 01/77107 | 10/2001 |
| WO | WO 03/031442 | 4/2003 |
| WO | WO 03/059907 | 7/2003 |

OTHER PUBLICATIONS

Freshney (Culture of Animal Cells, A Manual of Basic Technique, Alan R. Liss, Inc., 1983, New York, p. 4).*
Dermer (Biocechnology, 1994, 12:320).*
Baselga, J. et al., Oncology 63 (Suppl. 1) 2002, pp. 6-16.
Ranson, M. et al., Oncology 63 (Suppl 1) 2002 pp. 17-24.
Bernard Loubinoux, et al., J. Heterocyclic Chem., vol. 21, pp. 1669-1672 (1984).
J. Scott Sawyer, et al., Bioorganic & Medicinal Chemistry Letters, vol. 6, No. 3, pp. 249-252 (1996).
Pauline J. Sanfilippo, et al., Journal of Medicinal Chemistry, vol. 31, No. 9, pp. 1778-1785 (1988).

* cited by examiner

*Primary Examiner*—Kamal A. Saeed
*Assistant Examiner*—Michael P. Barker
(74) *Attorney, Agent, or Firm*—George W. Johnston; Patricia S. Rocha-Tramaloni

(57) ABSTRACT

The present invention 1 includes compounds of formula (I), formula (I)

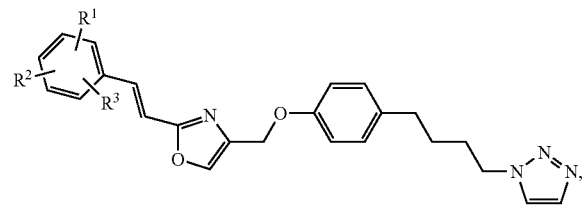

and their pharmaceutically acceptable salts. These compounds are useful in the control or prevention of cancer.

14 Claims, No Drawings

OXAZOLE DERIVATIVES

PRIORITY TO RELATED APPLICATIONS

This application claims the benefit of Provisional Application Ser. No. 60/459,741, filed Apr. 2, 2003.

FIELD OF THE INVENTION

The present invention relates to novel oxazole derivatives, to a process for their manufacture, pharmaceutical compositions containing these compounds, as well as the use of these compounds in the treatment of cancer.

BACKGROUND OF THE INVENTION

Protein tyrosine kinases (PTKs) catalyse the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394–401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443–478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer such as colon, rectal or stomach cancer, leukemia and ovarian, bronchial and pancreatic cancer. High levels of these receptors correlate with poor prognosis and response to treatment (Wright, C., et al., Br. J. Cancer 65 (1992) 118–121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6–16; Ranson, M., and Sliwkowski, M. X., Oncology 63 (suppl. 1) (2002) 17–24).

There remains a need for new receptor tyrosine kinase inhibitors with improved therapeutic properties, such as improved activity, solubility, tolerability, selectivity or stability to name only a few.

SUMMARY OF THE INVENTION

In one embodiment, the present invention relates to compounds of formula (I),

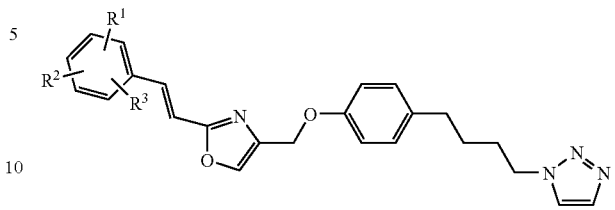

(I)

wherein
R$^1$ is selected from
—O-alkyl,
—S-alkyl, and
—NH-alkyl;
R$^2$ is selected from
hydrogen, and
halogen,
R$^3$ is hydrogen; or alternatively
R$^1$ and R$^2$ together with the carbon atoms to which they are attached form a 5 or 6 membered heterocyclic ring; and
R$^3$ is selected from
hydrogen and
halogen, or the pharmaceutically acceptable salt of the above compounds.

The compounds of the present invention are inhibitors of the HER-signalling pathway and therefore possess anti-proliferative activity. The compounds of the present invention include compounds of formula (I) and their pharmaceutically acceptable salts, enantiomeric forms, diastereoisomers and racemates. The present invention is also directed to methods of making the foregoing compounds, to pharmaceutical compositions containing these compounds as well as to the use of the above-mentioned compounds in the treatment or prevention of cancer, in particular, solid tumors, most particular the treatment or control of breast, lung, colon and prostate tumors. As used herein, the term "alkyl" means a saturated, straight-chain or branched-chain hydrocarbon containing from 1 to 4, preferably from 1 or 2, carbon atoms, such as methyl, ethyl, n-propyl, isopropyl, n-butyl, 2-butyl, t-butyl. Said alkyl group is optionally substituted with one or several halogen atoms, preferably fluorine. Examples are difluoromethyl, trifluoromethyl, 2,2,2-trifluoroethyl, perfluorethyl and the like.

The term "halogen" as used herein denotes fluorine, chlorine, bromine and iodine, preferably fluorine.

A "5 or 6 membered heterocyclic ring" as used herein means a monocyclic saturated or unsaturated hydrocarbon with 5 or 6 ring atoms of which 1 or 2 atoms are replaced by heteroatoms selected from S, N or O, preferably from N or O, and the remaining carbon-atoms, where possible, being optionally once or several times substituted with halogen, preferably fluorine. Preferably said "5 or 6 membered heterocyclic ring" is formed by R$^1$ and R$^2$ being located on two adjacent carbon-atoms of the phenyl ring to which they are attached. Examples of a "5 or 6 membered heterocyclic ring", including the phenyl ring to which it is attached, are benzo[1,3]dioxole, 2,2-difluoro-benzo[1,3]dioxole, 1H-benzoimidazole, 2,3-dihydro-benzo[1,4]dioxine, 3,4-dihydro-2H-benzo[1,4]oxazine, 1,3-dihydro-benzoimidazol-2-one and the like.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and quaternary ammonium hydroxides, such as for example, tetramethylammonium hydroxide. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Ansel, H., et. al., Pharmaceutical Dosage Forms and Drug Delivery Systems, 6th ed., 1995, at pp. 196 and 1456–1457.

Preferably, $R^1$ is selected from methoxy, difluoromethoxy, trifluoromethoxy and trifluoromethylsulfanyl.

In an embodiment, the invention is directed to compounds of formula (I), wherein
$R^1$ is —O-alkyl or
—S-alkyl;
$R^2$ is hydrogen; and
$R^3$ is hydrogen;

or the pharmaceutically acceptable salts thereof.

Such compounds include, for example:
1-[4-(4-{2-[2-(4-Methoxy-phenyl)-vinyl]-oxazol-4-ylmethoxy}-phenyl)-butyl]-1H-[1,2,3]triazole;
1-[4-(4-{2-[2-(4-Trifluoromethoxy-phenyl)-vinyl]-oxazol-4-ylmethoxy}-phenyl)-butyl]-1H-[1,2,3]triazole;
1-[4-(4-{2-[2-(4-Difluoromethoxy-phenyl)-vinyl]-oxazol-4-ylmethoxy}-phenyl)-butyl]-1H-[1,2,3]triazole; and
1-[4-(4-{2-[2-(4-Trifluoromethylsulfanyl-phenyl)-vinyl]-oxazol-4-ylmethoxy}-phenyl)-butyl]-1H-[1,2,3]triazole.

Another embodiment of the invention includes compounds of formula (I), wherein
$R^1$ is —O-alkyl or
—S-alkyl;
$R^2$ is halogen; and
$R^3$ is hydrogen;

or the pharmaceutically acceptable salts thereof.

Such a compound is for example:
1-[4-(4-{2-[2-(2-Fluoro-4-trifluoromethoxy-phenyl)-vinyl]-oxazol-4-ylmethoxy}-phenyl)-butyl]-1H-[1,2,3]triazole.

Another embodiment of the invention includes compounds of formula (I), wherein
$R^1$ and $R^2$ together with the carbon atoms to which they are attached form a 5 or 6 membered heterocyclic ring; and $R^3$ is hydrogen;
or their pharmaceutically acceptable salts.
Such compounds include, for example:
1-(4-{4-[2-(2-Benzo[1,3]dioxol-5-yl-vinyl)-oxazol-4-ylmethoxy]-phenyl}-butyl)-1H-[1,2,3]triazole;
1-[4-(4-{2-[2-(2,2-Difluoro-benzo[1,3]dioxol-5-yl)-vinyl]-oxazol-4-ylmethoxy}-phenyl)-butyl]-1H-[1,2,3]triazole; and
6-(2-{4-[4-(4-[1,2,3]Triazol-1-yl-butyl)-phenoxymethyl]-oxazol-2-yl}-vinyl)-1H-benzoimidazole.

Another embodiment of the invention includes compounds of formula (I), wherein
$R^1$ and $R^2$ together with the carbon atoms to which they are attached form a 5 or 6 membered heterocyclic ring; and
$R^3$ is halogen;

or their pharmaceutically acceptable salts.
Such compounds include, for example:
1-[4-(4-{2-[2-(2,2,6-Trifluoro-benzo[1,3]dioxol-5-yl)-vinyl]-oxazol-4-ylmethoxy}-phenyl)-butyl]-1H-[1,2,3]triazole; and
1-[4-(4-{2-[2-(2,2,4-Trifluoro-benzo[1,3]dioxol-5-yl)-vinyl]-oxazol-4-ylmethoxy}-phenyl)-butyl]-1H-[1,2,3]triazole Still another embodiment of the invention is a process for the manufacture of the compounds of formula (I), wherein
(a) a compound of formula (V)

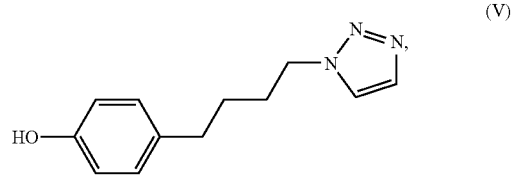

(V)

is reacted with a compound of formula (IV)

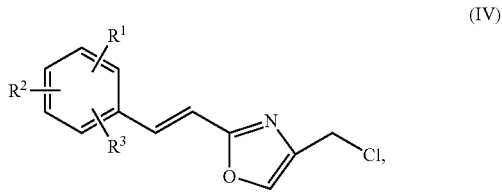

(IV)

wherein $R^1$, $R^2$ and $R^3$ have the significance given above, to give the respective compound of formula (I);
(b) said compound of formula (I) is optionally further isolated from the reaction mixture, and
(c) if desired, converted into a pharmaceutically acceptable salt.

The oxazole derivatives of the general formula (I), or a pharmaceutically acceptable salt thereof, may be prepared by any process known to be applicable for the preparation of chemically-related compounds by the one skilled in the art. Such processes, when used to prepare the oxazole derivatives of formula (I), or a pharmaceutically-acceptable salt thereof, are provided as a further feature of the invention and are illustrated by the following representative examples of scheme 1, in which, unless otherwise stated, $R^1$, $R^2$ and $R^3$ have the significance given herein before. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary

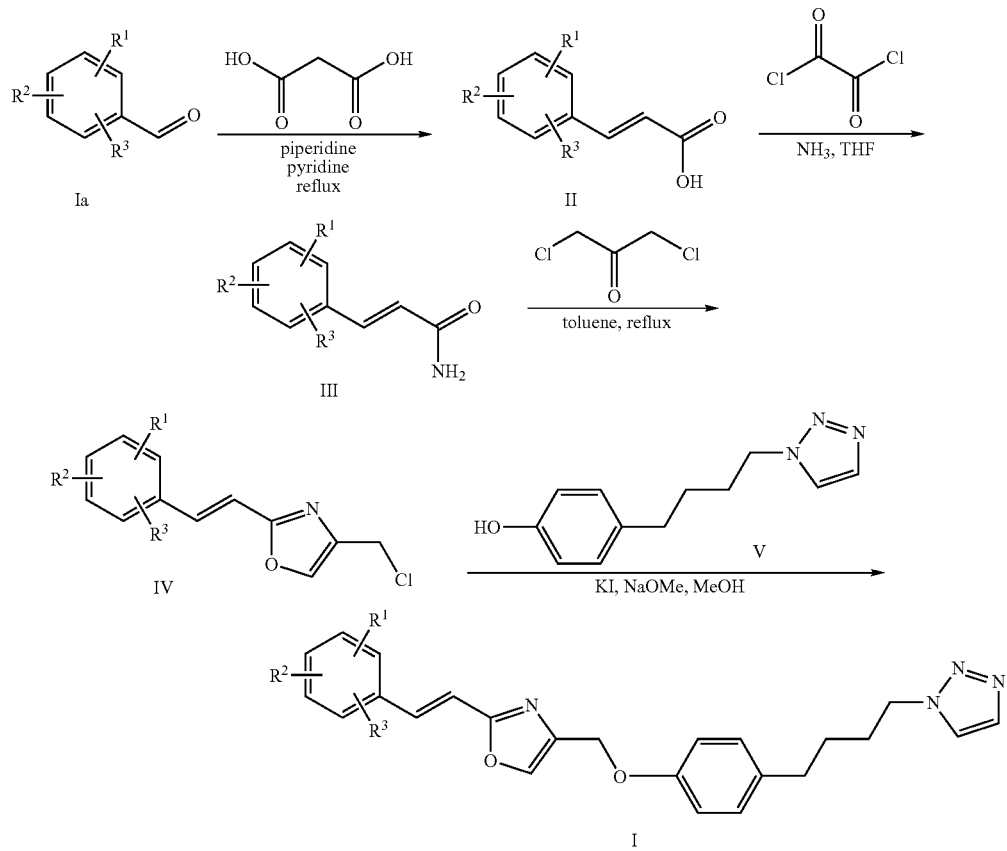

Scheme 1 skill of an organic chemist.

A preferred method for the synthesis of the compounds of the present invention starts from the corresponding benzaldehydes (Ia). The first step of the reaction sequence is a Knoevenagel condensation with malonic acid and concomitant decarboxylation, yielding acrylic acids of formula (II). The reaction is typically carried out in solvents like pyridine, N-Methylpyrrolidin, acetonitrile, N,N-dimethylformamide and mixtures thereof at temperatures up to 140° C. Typically used bases are piperidine, triethylamine and diisopropylamine.

The obtained acrylic acids of formula (II) are converted into their corresponding amides of formula (III) by standard methods for someone skilled in the art, e.g. by activating the carboxylic group in (II) with oxalyl chloride in solvents like tetrahydrofuran, dichloromethane, N,N-dimethylformamide and mixtures thereof at temperatures varying from −30° C. to 40° C. The addition of ammonia yields said amides of formula (III).

Chlorides of formula (IV) can be synthesized by a commonly known method or a modification thereof. Amides of formula (III) and 1,3-dichloroacetone are subjected to a condensation/dehydration sequence yielding the compounds of formula (IV). Typical solvents for reactions of this kind are toluene, benzene, acetone and chloroform. If desired the reaction can be carried out under solvent free conditions. The reaction temperatures may vary from 50° C. to 150° C.

The oxazole derivatives of formula (I) can be obtained by reactions well known to someone skilled in the art, e.g. by alkylation of 4-(4-[1,2,3]Triazol-1-yl-butyl)-phenol with compounds of formula (IV) according to scheme 1. Typically the alkylation is carried out in the presence of potassium iodide or sodium iodide in solvents like methanol, ethanol and isopropanol. Typical bases for this reaction are sodium methylate, sodium hydride, lithium diisopropyl amide or potassium carbonate/butanone. The reaction temperatures may vary from 50° C. to 150° C.

The compounds of formula (I) can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds of formula (I) and their pharmaceutically acceptable salts possess valuable pharmacological properties. It has been found that said compounds inhibit the HER-signalling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above.

The activity of the present compounds as HER-signalling pathway inhibitors is demonstrated by the following biological assay:

Material and Methods

Cell Culture Setup

A squamous cell carcinoma cell line (e.g. QG 56) was cultivated in DMEM/10%FCS/2 mM glutamine at about 60% confluency. Exponentially growing cells were seeded at a density of $1 \times 10^4$ cells/cm$^2$ in 2 ml of medium per 6 wells. After 24 hours medium was replaced and compounds were added.

For the BrdU/Hoechst quenching assay the media were supplemented with $8 \times 10^{-5}$ BrdU and deoxycytidine, respectively. All experiments were performed in 6 well culture plates.

Experimental Setup

The cell culture setup is as described above. All compounds were dissolved in DMSO at a concentration of 10 mM.

Adherent cells were harvested at 24 h by trypsinization and cells from the supernatant were added to the population.

Cell Kinetic FACS Analysis

After centrifugation cell pellets were resuspended at $1-10 \times 10^5$ cells/ml in DNA-staining puffer (100 mM Tris pH 7.4, 154 mM NaCl, 1 mM CaCl$_2$, 0.5 mM MgCl$_2$, 0.2% BSA, 0.1% NP40) supplemented with 5 ug/ml RNAse A and 1.5 ug/ml Hoechst 33258. After 15 min propidium iodide was added to a final concentration of 1.5 ug/ml for another 15 min. The fluorochrome labeled cells were analysed on a flow cytometer (BD LSR) applying dual laser excitation (UV and 488 nm). The quenched Hoechst 33258 and the BrdU unaffected PI fluorescence were displayed on a 2D plot on the X- and Y-axis, respectively.

Results

Compounds of Example 1, Example 2 and Example 4 were tested at a concentration of 3 µM.

Results extracted from BrdU-Hoechst dot plots after incubation for 24 h are shown in Table 1. With all compounds a G1 cell cycle arrest was observed, with compounds from examples 1, 2 and 4 showing a higher percentage of QG56 cells arrested in the first G1 phase than with 1-[4-(4-{2-[2-(4-Trifluoromethyl-phenyl)-vinyl]-oxazol-4-yl-methoxy}-phenyl)-butyl]-1H-[1,2,3]triazole (Example 4, p. 88, WO 01/77107) as reference compound.

TABLE 1

|  | Control (DMSO) | n-fold increase of cells arrested in first cell cycle (compound concentration 3 µM) |
|---|---|---|
| reference compound | 1 | 17.2 |
| example 1 | 1 | 23.7 |
| example 2 | 1 | 19.2 |
| example 4 | 1 | 17.9 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical compositions comprise the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

Pharmaceutical compositions including at least one compound of formula (I), or a pharmaceutically acceptable salt thereof, and a therapeutically inert carrier are also an object of the present invention, as is a process for their production, which comprises bringing one or more compounds of formula (I) and/or pharmaceutically acceptable salts and, if desired, one or more other therapeutically valuable substances into a galenical administration form together with one or more therapeutically inert carriers.

In accordance with the invention, compounds of formula (I) as well as their pharmaceutically acceptable salts are useful in the control or prevention of illnesses. Based on their HER-signalling pathway inhibition and their antiproliferative activity, said compounds are useful for the treatment of diseases such as cancer in humans or animals. The dosage of a compound of formula I, or its pharmaceutically acceptable salt, required for treatment or control (that is the "therapeutically effective amount") depends on various factors such as manner of administration, as well as species, size, age and/or individual state of health of the patient. In general, in the case of oral parenteral administration to adult humans weighing approximately 70 kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as a continuous infusion.

The following examples are provided to aid the understanding of the present invention, the true scope of which is set forth in the appended claims. It is understood that modifications can be made in the procedures set forth without departing from the spirit of the invention.

EXAMPLE 1

1-[4-(4-{2-[2-(4-Methoxy-phenyl)-vinyl]-oxazol-4-ylmethoxy}-phenyl)-butyl]-1H-[1,2,3]triazole 44.5 ml (351 mmol) oxalyl chloride was added dropwise at 0° C. within 45 min. to a suspension of 50.0 g (281 mmol) 3-(4-Methoxyphenyl)-acrylic acid in 300 ml tetrahydrofuran and 3.0 ml N,N-dimethyl formamide. Stirring was continued at 0–5° C. for 30 min. and thereafter for 2 h at room temperature. The resulting solution was cooled to 0–5° C. again and then added within 15 min. to 750 ml of a 25% aqueous solution of ammonia. After stirring for 30 min. the precipitated amide was collected, washed with water and dried at 40° C. in vacuo. 48.8 g (98%) 3-(4-Methoxyphenyl)-acrylamide were obtained.

MS: M=178.2 (API+). $^1$H-NMR(400 MHz, $D_6$-DMSO): δ=3.79(s, 1H, $OCH_3$), 6.46(d, 1H, 2-H), 6.97(d, 2H, 3'-/5'-H), 6.99(br, 1H, NH), 7.36(d, 1H, 3-H), 7.44(br, 1H, NH), 7.50(d, 2H, 2'-/6'-H). 48.0 g (271 mmol) 3-(4-Methoxyphenyl)-acrylamide, 44.4 g (350 mmol) dichloro acetone and 400 ml toluene were kept at reflux temperature for 24 h with continuous removal of water by applying a Dean-Stark trap. After removal of solvents in vacuo, the residue was intensively shaken with 600 ml water, the precipitate isolated by filtration, washed with water and heptane. Drying at 40° C. in vacuo gave 56.9 g (84%) 4-Chloromethyl-2-[2-(4-methoxyphenyl)-vinyl]-oxazole.

MS: M=250.2 (API+). $^1$H-NMR(400 MHz, $D_6$-DMSO): δ=3.80(s, 3H, $OCH_3$), 4.69(s, 2H, $CH_2Cl$), 6.98(d, 2H, Ar—H), 7.00(d, 1H, =CH), 7.49(d, 1H, =CH), 7.67(d, 2H, Ar—H), 8.13(s, 1H, oxazole). 0.250 g (1.00 mmol) 4-Chloromethyl-2-[2-(4-methoxyphenyl)-vinyl]-oxazole, 0.217 g 1.00 mmol) 4-(4-[1,2,3]Triazol-1-yl-butyl)-phenol, 0.166 g (1.00 mmol) potassium iodide and 0.191 ml (1.00 mmol) of a 30% sodium methylate solution were added to 50.0 ml methanol and heated to reflux for 8 h. After removal of solvent, partitioning of the residue between 50 ml ethyl acetate and 15 ml water, the organic phase was washed with 10 ml water, 10 ml 0.1 N NaOH, 15 ml water twice and dried over sodium sulphate. The solution was concentrated until crystallisation of the product started. After leaving for 1 h at room temperature the precipitate was isolated, washed with diethyl ether and dried at 40° C. in vacuo. 0.16 g (37%) 1, m.p. 148–151° C.

MS: M=431.3 (API+), M=429.3 (API–). $^1$H-NMR(400 MHz, $D_6$-DMSO): δ=1.48(quintet, 2H, C$\underline{H}_2$—CH2-Ph), 1.81(quintet, 2H, C$\underline{H}_2$—CH2-N), 2.53(t, 2H, $CH_2$-Ph), 3.80 (s, 3H, $OCH_3$), 4.39(t, 2H, $CH_2$-triazole), 4.96(s, 2H, $OCH_2$-oxazole), 6.9–7.1(m, 7H), 7.09(d, 1H, =CH), 7.66(d, 2H, 3"-/5"-H), 7.71(s, 1H, oxazole), 8.11(s, 1H, triazole), 8.14(s, 1H, triazole).

EXAMPLE 2

1-[4-(4-{2-[2-(4-Trifluoromethoxy-phenyl)-vinyl]-oxazol-4-ylmethoxy}-phenyl)-butyl]-1H-[1,2,3]triazole A mixture of 5.00 g (3.80 ml, 26.3 mmol) 4-Trifluoromethoxy-benzaldehyde, 3.10 g (30.0 mmol) malonic acid, 0.26 g (3.0 mmol) piperidine and 15.0 ml pyridine was kept at reflux temperature until carbon dioxide development ceased (3 h). After cooling to room temperature the reaction mixture was poured onto 50 g ice and 15 ml 6N HCl. The precipitate was isolated, washed with water and dried. Yield: 5.20 g (85%) 3-(4-Trifluoromethoxy-phenyl)-acrylic acid.

$^1$H-NMR(400 MHz, $D_6$-DMSO): δ=6.57(d, 1H, 2-H), 7.40(d, 2H, 3'-/5'-H), 7.62(d, 1H, 3-H), 7.84(d, 2H, 2'-/6'-H), 12.5(br, 1H, COOH).

To a suspension of 4.90 g (21.1 mmol) 3-(4-Trifluoromethoxy-phenyl)-acrylic acid in 30.0 ml tetrahydrofuran and 0.3 ml N,N-dimethyl formamide a solution of 2.70 ml (32.0 mmol) oxalyl chloride in 5.0 ml tetrahydrofuran was added dropwise at 0° C. within 10 min. Stirring was continued at 0–5° C. for 30 min. and 2 h at room temperature thereafter. The resulting solution was cooled to 0–5° C. again and then added within 15 min. to 75 ml of a 25% aqueous ammonia solution. After stirring for 30 min. the precipitated amide was collected, washed with water and dried at 40° C. in vacuo. 4.48 g (92%) 3-(4-Trifluoromethoxy-phenyl)-acrylamide.

MS: M=232.2(API+) $^1$H-NMR(400 MHz, $D_6$-DMSO): δ=6.63(d, 1H, 2-H), 7.16(br, 1H, NH), 7.42(d, 2H, 3'-/5'-H), 7.45(d, 1H, 3-H), 7.58(br, 1H, NH), 7.70(d, 2H, 2'-/6'-H). 4.28 g (18.5 mmol) 3-(4-Trifluoromethoxy-phenyl)-acrylamide, 2.80 g (22.2 mmol) dichloro acetone and 30.0 ml toluene were kept at reflux temperature for 16 h with continuous removal of water by use of a Dean-Stark trap. After removal of solvents in vacuo, the residue was purified by chromatography on silica gel (eluent: heptane/ethyl acetate 20:1). All fractions containing the product were concentrated to a volume of 10 ml and the crystallised material isolated by filtration, washed with cold heptane and dried. 1.75 g (31%) 4-Chloromethyl-2-[2-(4-trifluoromethoxy-phenyl)-vinyl]-oxazole.

MS: M=304.2(API+). $^1$H-NMR(400 MHz, $D_6$-DMSO): δ=4.71(s, 2H, $CH_2Cl$), 7.21(d, 1H, =CH), 7.40(d, 2H, Ar—H), 7.58(d, 1H, =CH), 7.87(d, 2H, Ar—H), 8.19(s, 1H, oxazole). 0.304 g (1.00 mmol) 4-Chloromethyl-2-[2-(4-trifluoromethoxy-phenyl)-vinyl]-oxazole, 0.217 g (1.00 mmol) 4-(4-[1,2,3]Triazol-1-yl-butyl)-phenol, 0.166 g (1.00 mmol) potassium iodide and 0.191 ml (1.00 mmol) of a 30% sodium methylate solution were added to 50.0 ml methanol and heated to reflux for 8 h. After removal of solvent, partitioning of the residue between 50 ml ethyl acetate and 15 ml water, the organic phase was washed with 10 ml water, 10 ml 0.1 N NaOH, 15 ml water twice and dried over sodium sulphate. The solution was concentrated until crystallisation of the product started. After leaving for 1 h at room temperature the precipitate was isolated, washed with ether and dried at 40° C. in vacuo. Yield 0.16 g (32%) 2, m.p. 138–140° C.

MS: M=487.3 (API+), M=485.2 (API−). $^1$H-NMR(400 MHz, D$_6$-DMSO): δ=1.48(quintet, 2H, C$\underline{H}_2$—CH2-Ph), 1.81(quintet, 2H, C$\underline{H}_2$—CH2-N), 2.53(t, 2H, CH$_2$-Ph), 4.39 (t, 2H, CH$_2$-triazole), 4.98(s, 2H, OCH$_2$-oxazole), 6.94(d, 2H, 3'-,5'-H), 7.09(d, 2H, 2'-,6'-H), 7.21(d, 1H, =CH), 7.40(d, 2H, Ar—H), 7.56(d, 1H, =CH), 7.70(s, 1H, oxazole), 7.86(d, 2H, Ar—H), 8.11(s, 1H, triazole), 8.20(s, 1H, triazole).

EXAMPLE 3

1-[4-(4-{2-[2-(4-Difluoromethoxy-phenyl)-vinyl]-oxazol-4-ylmethoxy}-phenyl)-butyl]-1H-[1,2,3]triazole A mixture of 10.0 g (7.68 ml, 58.1 mmol) 4-Difluoromethoxy-benzaldehyde, 6.65 g (63.9 mmol) malonic acid, 0.21 g (2.50 mmol) piperidine and 50 ml pyridine was kept at reflux temperature until carbon dioxide development ceased (3 h). After cooling to room temperature the reaction mixture was poured onto 200 g ice and 100 ml 6N HCl. The precipitate was isolated, washed with water and dried. Yield: 8.8 g (71%) 3-(4-Difluoromethoxy-phenyl)-acrylic acid.

$^1$H-NMR(400 MHz, D$_6$-DMSO): δ=6.51(d, 1H, 2-H), 7.21(d, 2H, 3'-/5'-H), 7.32(t, 1H, OCHF$_2$), 7.59(d, 1H, 3-H), 7.77(d, 2H, 2'-/6'-H), 12.4(br, 1H, COOH).

To a suspension of 8.70 g (40.6 mmol) 3-(4-Difluoromethoxy-phenyl)-acrylic acid in 60.0 ml tetrahydrofuran and 0.6 ml N,N-dimethyl formamide a solution of 5.14 ml (60.9 mmol) oxalyl chloride in 10 ml tetrahydrofuran was added dropwise at 0° C. within 10 min. Stirring was continued at 0–5° C. for 30 min. and 2 h at room temperature thereafter. The resulting solution was cooled to 0–5° C. again and then added within 15 min. to 150 ml of a 25% aqueous ammonia solution. The separating oil was collected and stirred for 30 min. with water. The precipitated amide was collected, washed with water and dried at 40° C. in vacuo. 4.7 g (54%) 3-(4-Difluoromethoxy-phenyl)-acrylamide.

MS: M=214.2 (API+). $^1$H-NMR(400 MHz, D$_6$-DMSO): δ=6.57(d, 1H, 2-H), 7.10(br, 1H, NH), 7.21(d, 2H, 3'-/5'-H), 7.29(t, 1H, CHF$_2$), 7.45(d, 1H, 3-H), 7.53(br, 1H, NH), 7.63(d, 2H, 2'-/6'-H). 4.50 g (21.1 mmol) 3-(4-Difluoromethoxy-phenyl)-acrylamide, 3.20 g (25.2 mmol) dichloro acetone and 45 ml toluene were kept at reflux temperature for 22 h with continuous removal of water by use of a Dean-Stark trap. After removal of solvents in vacuo, the residue was stirred with diethyl ether, the precipitation (some remaining starting material) sucked off and the filtrate evaporated to dryness. The residue was extracted three times with heptane, the heptane fractions evaporated and the residue dried in vacuo. 1.0 g (16%) 4-Chloromethyl-2-[2-(4-difluoromethoxy-phenyl)-vinyl]-oxazole.

MS: M=286.2(API+). $^1$H-NMR(400 MHz, D$_6$-DMSO): δ=4.70(s, 2H, CH$_2$Cl, 7.14(d, 1H, =CH), 7.22(d, 2H, Ar—H), 7.31(t, 1H, OCHF$_2$), 7.54(d, 1H, =CH), 7.80(d, 2H, Ar—H), 8.17(s, 1H, oxazole).

0.286 g (1.00 mmol) 4-Chloromethyl-2-[2-(4-difluoromethoxy-phenyl)-vinyl]-oxazole, 0.217 g 1.00 mmol) 4-(4-[1,2,3]Triazol-1-yl-butyl)-phenol, 0.166 g (1.00 mmol) potassium iodide and 0.191 ml (1.00 mmol) of a 30% sodium methylate solution were added to 50.0 ml methanol and heated to reflux for 12 h. After removal of solvent, partitioning of the residue between 50 ml ethyl acetate and 15 ml water, the organic phase was washed with 10 ml water, 10 ml 0.1 N NaOH, 15 ml water twice and dried over sodium sulphate. The solution was concentrated to a volume of 5 ml until crystallisation of the product started. After leaving for 1 h at room temperature the precipitate was sucked off, washed with ether and dried at 40° C. in vacuo. Yield 0.20 g (43%) 3.

MS: M=467.3 (API+). $^1$H-NMR(400 MHz, D$_6$-DMSO): δ=1.47(quintet, 2H, C$\underline{H}_2$—CH2-Ph), 1.80(quintet, 2H, C$\underline{H}_2$—CH2-N), 2.53(t, 2H, CH$_2$-Ph), 4.38(t, 2H, CH$_2$-triazole), 4.97(s, 2H, OCH$_2$-oxazole), 6.94(d, 2H, 3'-,5'-H), 7.10 (d, 2H, 2'-,6'-H), 7.12(d, 1H, =CH), 7.30(t, 1H, OCHF$_2$), 7.21(d, 2H, Ar—H), 7.30(t, 1H, OCHF$_2$), 7.53(d, 1H, =CH), 7.70(s, 1H, oxazole), 7.79(d, 2H, Ar—H), 8.10(s, 1H, triazole), 8.18(s, 1H, triazole).

EXAMPLE 4

1-(4-{4-[2-(2-Benzo[1,3]dioxol-5-yl-vinyl)-oxazol-4-ylmethoxy]-phenyl}-butyl)-1H-[1,2,3]triazole To a suspension of 50.0 g (260 mmol) 3-Benzo[1,3]dioxol-5-yl-acrylic acid in 300 ml tetrahydrofuran and 3.0 ml N,N-dimethyl formamide 44.5 ml (350 mmol) oxalyl chloride was added dropwise at 0° C. within 45 min. Stirring was continued at 0–5° C. for 30 min. and 2 h at room temperature thereafter. The resulting solution was cooled to 0–5° C. again and then added within 15 min. to 750 ml of an 25% aqueous solution of ammonia. After stirring for 30 min. the precipitated amide was collected, washed with water and dried at 40° C. in vacuo. 49.5 g (99%) 3-Benzo[1,3]dioxol-5-yl-acrylamide were obtained.

MS: M=192.2 (API+). $^1$H-NMR(400 MHz, D$_6$-DMSO): δ=6.06(s, 2H, OCH$_2$O), 6.45(d, 1H, 2-H), 6.94(d, 1H, 7'-H), 7.02(br, 1H, NH), 7.05(d, 1H, 6'-H), 7.14(s, 1H, 4'-H), 7.33(d, 1H, 3-H), 7.42(br, 1H, NH).

49.0 g (256 mmol) 3-Benzo[1,3]dioxol-5-yl-acrylamide, 44.4 g (350 mmol) dichloro acetone and 300 ml toluene were kept at reflux temperature for 48 h with continuous removal of water by applying a Dean-Stark trap. After removal of solvents in vacuo, the residue was treated with 600 ml of a 1:1 mixture of water/isopropanol. After filtration the precipitate was washed first with isopropanol, then with heptane. Drying at 40° C. in vacuo gave 51.2 g (76%) 2-(2-Benzo[1,3]dioxol-5-yl-vinyl)-4-chloromethyl-oxazole.

$^1$H-NMR(400 MHz, D$_6$-DMSO): δ=4.69(s, 2H, CH$_2$Cl), 6.07(s, 2H, OCH$_2$O), 6.94(d, 1H, 7'-H), 7.02(d, 1H, 2-H), 7.17(d, 1H, 6'-H), 7.43(s, 1H, 4'-H), 7.45(d, 1H, 3-H), 7.70(br, 1H, NH), 7.98(br, 1H, NH), 8.13(s, 1H, oxazole).

0.264 g (1.00 mmol) 2-(2-Benzo[1,3]dioxol-5-yl-vinyl)-4-chloromethyl-oxazole, 0.217 g 1.00 mmol) 4-(4-[1,2,3]Triazol-1-yl-butyl)-phenol, 0.166 g (1.00 mmol) potassium iodide and 0.191 ml (1.00 mmol) of a 30% sodium methylate solution were added to 50.0 ml methanol and heated to reflux for 8 h. After removal of solvent, partitioning of the residue between 50 ml ethyl acetate and 15 ml water, the organic phase was washed with 10 ml water, 10 ml 0.1 N NaOH, 15 ml water twice and dried over sodium sulphate. The solution was concentrated to a volume until crystallisation of the product started. After leaving for 1 h at room temperature the precipitate was filtered, washed with diethyl ether and dried at 40° C. in vacuo. Yield 0.17 g (38%) 4.

MS: M=445.3 (API+), M=443.3 (API−). $^1$H-NMR(400 MHz, D$_6$-DMSO): δ=1.48(quintet, 2H, C$\underline{H}_2$—CH2-Ph), 1.81(quintet, 2H, C$\underline{\text{H}}_2$—CH2-N), 2.53(t, 2H, CH$_2$-Ph), 4.39 (t, 2H, CH$_2$-triazole), 4.96(s, 2H, OCH$_2$-oxazole), 6.07(s, 2H, OCH$_2$O), 6.9–7.2(m, 7H), 7.42(s, 1H, Ar—H), 7.44(d, 1H, =CH), 7.70(s, 1H, oxazole), 8.1 1(s, 1H, triazole), 8.14(s, 1H, triazole).

EXAMPLE 5

1-[4-(4-{2-[2-(4-Trifluoromethylsulfanyl-phenyl)-vinyl]-oxazol-4-ylmethoxy}-phenyl)-butyl]-1H-[1,2,3]triazole A mixture of 5.42 g (26.3 mmol) 4-Trifluoromethylsulfanyl-benzaldehyde, 3.12 g (30.0 mmol) malonic acid, 0.26 g (3.0 mmol) piperidine and 12.0 ml pyridine was kept at reflux temperature until carbon dioxide development ceased (5 h). After cooling to room temperature, the reaction mixture was poured onto 50 g ice and 15 ml 6N HCl. The precipitate was isolated, washed with water and dried. Yield: 5.90 g (90%) 3-(4-Trifluoromethylsulfanyl-phenyl)-acrylic acid.

$^1$H-NMR(400 MHz, D$_6$-DMSO): δ=6.65(d, 1H, 2-H), 7.63(d, 1H, 3-H), 7.74(d, 2H, 3'-/5'-H), 7.84(d, 2H, 2'-/6'-H), 12.7(br, 1H, COOH).

To a suspension of 5.24 g (21.1 mmol) 3-(4-Trifluoromethylsulfanyl-phenyl)-acrylic acid in 30.0 ml tetrahydrofuran and 0.3 ml N,N-dimethylformamide a solution of 2.70 ml (32.0 mmol) oxalyl chloride in 5.0 ml tetrahydrofuran was added dropwise at 0° C. within 20 min. Stirring was continued at 0–5° C. for 30 min. and 3 h at room temperature thereafter. The resulting solution was cooled to 0–5° C. again and then added within 15 min. to 100 ml of a 25% aqueous ammonia solution. After evaporation of the organic solvent, 200 ml water were added and the solution cooled. The precipitated amide was collected, washed with water and dried at 40° C. in vacuo. Yield 4.62 g (89%) 3-(4-Trifluoromethylsulfanyl-phenyl)-acrylamide.

MS: M=248.2(API+). $^1$H-NMR(400 MHz, D$_6$-DMSO): δ=6.72(d, 1H, 2-H), 7.21(br, 1H, NH), 7.46(d, 1H, 3-H), 7.62(br, 1H, NH), 7.73(dd, 4H, Ar—H).

4.45 g (18.0 mmol) 3-(4-Trifluoromethylsulfanyl-phenyl)-acrylamide, 2.80 g (22.2 mmol) 1,3-dichloro acetone and 50.0 ml toluene were kept at reflux temperature for 40 h with continuous removal of water by use of a Dean-Stark trap. After removal of solvents in vacuo, the residue was purified by chromatography on silica gel (eluent:heptane/ethyl acetate 1:1). All fractions containing the product were concentrated to a volume of 10 ml and the crystallised material isolated by filtration, washed with cold heptane and dried. Yield 2.02 g (35%) 4-Chloromethyl-2-[2-(4-trifluoromethylsulfanyl-phenyl)-vinyl]-oxazole.

MS: M=320.1(API+). $^1$H-NMR(400 MHz, D$_6$-DMSO): δ=4.71(s, 2H, CH$_2$Cl), 7.30(d, 1H, =CH), 7.59(d, 1H, =CH), 7.74(d, 2H, Ar—H), 7.89(d, 2H, Ar—H), 8.21(s, 1H, oxazole).

0.32 g (1.00 mmol) 4-Chloromethyl-2-[2-(4-trifluoromethylsulfanyl-phenyl)-vinyl]-oxazole, 0.217 g (1.00 mmol) 4-(4-[1,2,3]Triazol-1-yl-butyl)-phenol, 0.166 g (1.00 mmol) potassium iodide and 0.191 ml (1.00 mmol) of sodium methylate (30% in methanol) were added to 50.0 ml methanol and heated to reflux for 16 h. After removal of solvent and partitioning of the residue between 50 ml ethyl acetate and 15 ml water, the organic phase was washed with 10 ml water, 10 ml 0.1 N NaOH and twice 15 ml water, and dried over sodium sulfate. The solution was concentrated until crystallisation of the product started. After leaving for 1 h at room temperature the precipitate was isolated, washed with ether and dried at 40° C. in vacuo. Yield 0.11 g (18%) 1-[4-(4-{2-[2-(4-Trifluoromethylsulfanyl-phenyl)-vinyl]-oxazol-4-ylmethoxy}-phenyl)-butyl]-1H-[1,2,3]triazole, m.p. 144–145° C.

MS: M=501.2 (API+). $^1$H-NMR(400 MHz, D$_6$-DMSO): δ=1.49(quintet, 2H, C$\underline{\text{H}}_2$—CH2-Ph), 1.81(quintet, 2H, C$\underline{\text{H}}_2$—CH$_2$-N), 2.54(t, 2H, CH$_2$-Ph), 4.32(t, 2H, CH$_2$-triazole), 4.99(s, 2H, OCH$_2$-oxazole), 6.94(d, 2H, 3'-,5'-H), 7.10 (d, 2H, 2'-,6'-H), 7.31(d, 1H, =CH), 7.59(d, 1H, =CH), 7.71(s, 1H, oxazole), 7.74(d, 2H, Ar—H), 7.89(d, 2H, Ar—H), 8.11(s, 1H, triazole), 8.23(s, 1H, triazole).

EXAMPLE 6

1-[4-(4-{2-[2-(2,2-Difluoro-benzo[1,3]dioxol-5-yl)-vinyl]-oxazol-4-ylmethoxy}-phenyl)-butyl]-1H-[1,2,3]triazole A mixture of 10.0 g (53.7 mmol) 2,2-Difluoro-benzo[1,3]dioxole-5-carbaldehyde, 6.24 g (60.0 mmol) malonic acid, 0.46 g (5.40 mmol) piperidine and 40 ml pyridine was kept at reflux temperature until carbon dioxide development ceased (3 h). After cooling to room temperature the reaction mixture was poured onto 100 g ice and 30 ml 6N HCl. The precipitate was isolated, washed with water and dried. Yield: 8.60 g (70%) 3-(2,2-Difluoro-benzo[1,3]dioxol-5-yl)-acrylic acid.

To a suspension of 8.00 g (35.1 mmol) 3-(2,2-Difluoro-benzo[1,3]dioxol-5-yl)-acrylic acid in 40 ml tetrahydrofurane and 0.4 ml N,N-dimethyl formamide, 3.86 ml (45.0 mmol) oxalyl chloride was added dropwise at 0° C. within 10 min. Stirring was continued at 0–5° C. for 30 min. and 2 h at room temperature thereafter. The resulting solution was cooled to 0–5° C. again and then added within 15 min. to 34 ml of an 25% aqueous solution of ammonia. After stirring for 30 min. the precipitated amide was collected, washed with water and dried at 40° C. in vacuo. 7.20 g (90%) 3-(2,2-Difluoro-benzo[1,3]dioxol-5-yl)-acrylamide were obtained.

$^1$H-NMR(400 MHz, D$_6$-DMSO): δ=6.59(d, 1H, 2-H), 7.14(br, 1H, NH), 7.41–7.46(m, 3H, 3-H/7'-H/6'-H), 7.53(br, 1H, NH), 7.66(s, 1H, 4'-H).

6.90 g (30.4 mmol) 3-(2,2-Difluoro-benzo[1,3]dioxol-5-yl)-acrylamide, 4.76 g (37.5 mmol) 1,3-dichloro acetone and 50 ml toluene were kept at reflux temperature for 48 h with continuous removal of water by applying a Dean-Stark trap. After removal of solvents in vacuo, the residue was treated with 60 ml of a 1:1 mixture of water/isopropanol. After filtration the precipitate was washed first with isopropanol, then with heptane. Drying at 40° C. in vacuo gave 4-Chloromethyl-2-[2-(2,2-difluoro-benzo[1,3]dioxol-5-yl)-vinyl]-oxazole.

MS: M=300.0 (API+). $^1$H-NMR(400 MHz, D$_6$-DMSO): δ=4.70(s, 2H, CH$_2$Cl), 7.20(d, 1H, 2-H), 7.45(d, 1H, 7'-H), 7.55(d, 1H, 3-H), ), 7.56(d, 1H, 6'-H), 7.92(s, 1H, 4'-H), 8.18(s, 1H, oxazole).

To a solution of 0.217 g (1.00 mmol) 4-(4-[1,2,3]Triazol-1-yl-butyl)-phenol in 4 ml N,N-dimethyl formamide 40 mg (1.00 mmol) of NaH (60% dispersion in mineral oil) were added and the mixture stirred for 15 min at room temperature. Subsequently 0.3 g (1.00 mmol) 4-chloromethyl-2-[2-(2,2-difluoro-benzo[1,3]dioxol-5-yl)-vinyl]-oxazole were added and stirring continued for 12 h. 20 ml of water were added, the resulting precipitate collected, washed with water (2×), methanol/water (1:1), ether (3×) and dried in vacuo yielding 0.42 g (87%) 1-[4-(4-{2-[2-(2,2-Difluoro-benzo[1, 3]dioxol-5-yl)-vinyl]-oxazol-4-ylmethoxy}-phenyl)-butyl]-1H-[1,2,3]triazole as white solid.

$^1$H-NMR(400 MHz, D$_6$-DMSO): δ=1.48(quintet, 2H, CH$_2$—CH2-Ph), 1.81(quintet, 2H, CH$_2$—CH$_2$-N), 2.53(t, 2H, CH$_2$-Ph), 4.39(t, 2H, CH$_2$-triazole), 4.97(s, 2H, OCH$_2$-oxazole), 6.94(d, 2H, 3'-,5'-H), 7.09(d, 2H, 2'-,6'-H), 7.20(d, 1H, =CH), 7.45(d, 1H), 7.54(m, 2H), 7.70(s, 1H), 7.92 (s, 1H), 8.11(s, 1H, triazole), 8.19(s, 1H, triazole).

EXAMPLE 7

1-[4-(4-{2-[2-(4-Trifluoromethoxy-phenyl)-vinyl]-oxazol-4-ylmethoxy}-phenyl)-butyl]-1H-[1,2,3]triazolium methanesulfonate 12.1 g (25 mmol) 1-[4-(4-{2-[2-(4-Trifluoromethoxy-phenyl)-vinyl]-oxazol-4-ylmethoxy}-phenyl)-butyl]-1H-[1,2,3]triazole were dissolved in 150 ml tetrahydrofuran at 50° C., cooled to room temperature, treated with 1.625 ml (25 mmol) methanesulfonic acid and stirred for 1h. After the addition of 300 ml diethyl ether stirring was continued for 1 h, the precipitate collected and washed with diethyl ether. Drying over phosphorus pentoxide yielded 12.4 g (85%) 1-[4-(4-{2-[2-(4-Trifluoromethoxy-phenyl)-vinyl]-oxazol-4-ylmethoxy}-phenyl)-butyl]-1H-[1,2,3]triazolium methanesulfonat.

$^1$H-NMR(400 MHz, D$_4$-methanol): δ=1.64 (quintet, 2H, CH$_2$—CH2-Ph), 1.99(quintet, 2H, CH$_2$—CH2-N), 2.64(t, 2H, CH$_2$-Ph), 2.72(s, 3H, CH$_3$), 4.57(t, 2H, CH$_2$-triazole), 5.02 (s, 2H, OCH$_2$-oxazole), 6.95(d, 2H, 3'-,5'-Ar—H), 7.08(d, 1H, vinyl-H), 7.13(d, 2H, 2'-6'-Ar—H), 7.34(d, 2H, ArOCF$_3$), 7.62(d, 1H, vinyl-H), 7.76(d, 2H, ArOCF$_3$), 7.98 (s, 1H, oxazole), 8.11(s, 1H, triazole), 8.27(s, 1H, triazole).

EXAMPLE 8

1-[4-(4-{2-[2-(4-Trifluoromethoxy-phenyl)-vinyl]-oxazol-4-ylmethoxy}-phenyl)-butyl]-1H-[1,2,3]triazolium p-toluenesulfonate To a solution of 0.124 g (0.26 mmol) 1-[4-(4-{2-[2-(4-Trifluoromethoxy-phenyl)-vinyl]-oxazol-4-ylmethoxy}-phenyl)-butyl]-1H-[1,2,3]triazole in 20 ml EtOH 0.973 μl (50 mg/ml in EtOH) of p-toluenesulfonic acid was added and heated to 60° C. for complete dissolution. After evaporation of the solvent the oily residue crystallized slowly to yield 1-[4-(4-{2-[2-(4-Trifluoromethoxy-phenyl)-vinyl]-oxazol-4-ylmethoxy}-phenyl)-butyl]-1H-[1,2,3]triazolium p-toluenesulfonate.

$^1$H-NMR(400 MHz, D$_6$-DMSO): δ=1.48(quintet, 2H, CH$_2$—CH2-Ph), 1.81(quintet, 2H, CH$_2$—CH$_2$-N), 2.29 (s, 3H), 2.53(t, 2H, CH$_2$-Ph), 4.40(t, 2H, CH$_2$-triazole), 4.97(s, 2H, OCH$_2$-oxazole), 7.09 (d, 2H), 7.11 (d, 2H), 7.21 (d, 1H), 7.41 (d, 2H), 7.48 (d, 2H), 7.57 (d, 1H), 7.72 (s, 1H, NH), 7.88 (d, 2H), 7.94 (d, 2H), 8.13 (s, 1H, triazole), 8.21 (s, 1H, triazole).

EXAMPLE 9

1-[4-(4-{2-[2-(4-Trifluoromethoxy-phenyl)-vinyl]-oxazol-4-ylmethoxy}-phenyl)-butyl]-1H-[1,2,3]triazolium chloride 75 mg (0.13 mmol) 1-[4-(4-{2-[2-(4-Trifluoromethoxy-phenyl)-vinyl]-oxazol-4-ylmethoxy}-phenyl)-butyl]-1H-[1,2,3]triazole were dissolved in a mixture of 5 ml ethyl acetate and 1 ml tetrahydrofuran. HCl gas was bubbled through the solution for 30 s followed by stirring at 80° C. for 1 h. After cooling the precipitate was collected and dried in vacuo yielding 1-[4-(4-{2-[2-(4-Trifluoromethoxy-phenyl)-vinyl]-oxazol-4-ylmethoxy}-phenyl)-butyl]-1H-[1,2,3]triazolium chloride.

$^1$H-NMR(400 MHz, D$_6$-DMSO): δ=1.48(quintet, 2H, CH$_2$—CH2-Ph), 1.81(quintet, 2H, CH$_2$—CH$_2$-N), 2.53(t, 2H, CH$_2$-Ph), 4.39(t, 2H, CH$_2$-triazole), 4.96(s, 2H, OCH$_2$-oxazole), 7.09 (d, 2H), 7.21 (d, 1H), 7.41 (d, 2H), 7.57 (d, 1H), 7.71 (s, 1H, NH), 7.88 (d, 2H), 7.94 (d, 2H), 8.12 (s, 1H, triazole), 8.21 (s, 1H, triazole).

The invention claimed is:
1. A compound of formula (I)

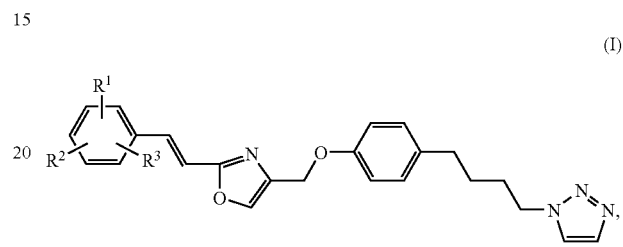

wherein
R$^1$ is selected from
—O-alkyl,
—S-alkyl, and
—NH-alkyl;
R$^2$ is selected from
hydrogen, and
halogen,
R$^3$ is hydrogen;
or alternatively
R$^1$ and R$^2$ together with the carbon atoms to which they are attached form a 5 or 6 membered heterocyclic ring; and
R$^3$ is selected from
hydrogen, and
halogen,
or a pharmaceutically acceptable salt thereof.

2. The compound of claim 1, wherein
R$^1$ is —O-alkyl or —S-alkyl;
R$^2$ is hydrogen; and
R$^3$ is hydrogen;
or a pharmaceutically acceptable salt thereof.

3. The compound of claim 2 selected from,
1-[4-(4-{2-[2-(4-Methoxy-phenyl)-vinyl]-oxazol-4-ylmethoxy}-phenyl)-butyl]-1H-[1,2,3]triazole;
1-[4-(4-{2-[2-(4-Trifluoromethoxy-phenyl)-vinyl]-oxazol-4-ylmethoxy}-phenyl)-butyl]-1H-[1,2,3]triazole;
1-[4-(4-{2-[2-(4-Difluoromethoxy-phenyl)-vinyl]-oxazol-4-ylmethoxy}-phenyl)-butyl]-1H-[1,2,3]triazole; and
1-[4-(4-{2-[2-(4-Trifluoromethylsulfanyl-phenyl)-vinyl]-oxazol-4-ylmethoxy}-phenyl)-butyl]-1H-[1,2,3]triazole.

4. The compound of claim 1, wherein
R$^1$ is —O-alkyl or —S-alkyl;
R$^2$ is halogen; and
R$^3$ is hydrogen;
or a pharmaceutically acceptable salt thereof.

5. The compound of claim 4, which is
1-[4-(4-{2-[2-(2-Fluoro-4-trifluoromethoxy-phenyl)-vinyl]-oxazol-4-ylmethoxy}-phenyl)-butyl]-1H-[1,2,3] triazole.

6. The compound of claim 1, wherein
$R^1$ and $R^2$ together with the carbon atoms to which they are attached form a 5 or 6 membered heterocyclic ring; and
$R^3$ is hydrogen;
or a pharmaceutically acceptable salt thereof.

7. The compound of claim 6 which is selected from
1-(4-{4-[2-(2-Benzo[1,3]dioxol-5-yl-vinyl)-oxazol-4-yl-methoxy]-phenyl}-butyl)-1H-[1,2,3]triazole;
1-[4-(4-{2-[2-(2,2-Difluoro-benzo[1,3]dioxol-5-yl)-vinyl]-oxazol-4-ylmethoxy}-phenyl)-butyl]-1H-[1,2,3]triazole; and
6-(2-{4-[4-(4-[1,2,3]Triazol-1-yl-butyl)-phenoxymethyl]-oxazol-2-yl}-vinyl)-1H-benzoimidazole.

8. The compound of claim 1, wherein
$R^1$ and $R^2$ together with the carbon atoms to which they are attached form a 5 or 6 membered heterocyclic ring; and
$R^3$ is halogen;
or a pharmaceutically acceptable salt thereof.

9. The compound of claim 8 which is selected from
1-[4-(4-{2-[2-(2,2,6-Trifluoro-benzo[1,3]dioxol-5-yl)-vinyl]-oxazol-4-ylmethoxy}-phenyl)-butyl]-1H-[1,2,3]triazole; and
1-[4-(4-{2-[2-(2,2,4-Trifluoro-benzo[1,3]dioxol-5-yl)-vinyl]-oxazol-4-ylmethoxy}-phenyl)-butyl]-1H-[1,2,3]triazole.

10. The compound of claim 1 which is selected from
1-[4-(4-{2-[2-(4-Trifluoromethoxy-phenyl)-vinyl]-oxazol-4-ylmethoxy}-phenyl)-butyl]-1H-[1,2,3]triazolium methanesulfonate,
1-[4-(4-{2-[2-(4-Trifluoromethoxy-phenyl)-vinyl]-oxazol-4-ylmethoxy}-phenyl)-butyl]-1H-[1,2,3]triazolium p-toluenesulfonate, and
1-[4-(4-{2-[2-(4-Trifluoromethoxy-phenyl)-vinyl]-oxazol-4-ylmethoxy}-phenyl)-butyl]-1H-[1,2,3]triazolium chloride.

11. A process for the manufacture of a compound of claim 1, wherein
(a) a compound of formula (V)

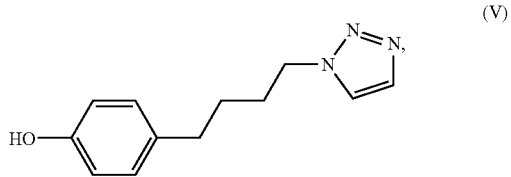

is reacted with a compound of formula (IV)

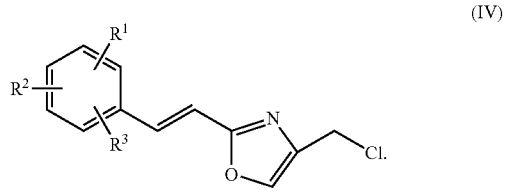

12. The process of claim 11 further comprising isolating the compound of formula (I) from the reaction mixture.

13. The process of claim 12 further comprising converting a compound of formula I to a pharmaceutically acceptable salt.

14. A pharmaceutical composition, comprising one or more compounds of claim 1 and a pharmaceutically acceptable excipient.

* * * * *